United States Patent [19]

Tcheng et al.

[11] Patent Number: 4,604,903

[45] Date of Patent: Aug. 12, 1986

[54] TWO-AXIS, SELF-NULLING SKIN FRICTION BALANCE

[75] Inventors: Ping Tcheng, Norfolk; Frank H. Supplee, Jr., Hampton, both of Va.

[73] Assignee: The United States of America as represented by the Administrator, National Aeronautics & Space Administration, Washington, D.C.

[21] Appl. No.: 706,681

[22] Filed: Feb. 28, 1985

[51] Int. Cl.[4] .............................................. G01L 5/16
[52] U.S. Cl. .................................. 73/862.04; 73/147; 73/862.61
[58] Field of Search ................. 73/147, 517 B, 862.04, 73/862.61

[56] References Cited

U.S. PATENT DOCUMENTS

| | | | |
|---|---|---|---|
| 3,224,263 | 12/1965 | Rogallo | 73/862.04 X |
| 3,304,775 | 2/1967 | Kistler | 73/147 |
| 3,415,116 | 12/1968 | Knechtel | 73/862.04 X |
| 3,490,059 | 1/1970 | Paulsen et al. | 73/862.04 |
| 3,699,811 | 10/1972 | Maiden et al. | |
| 4,059,011 | 11/1977 | Reiss | 73/862.04 X |
| 4,107,986 | 8/1978 | Jones | |
| 4,112,752 | 9/1978 | Hafner et al. | |
| 4,240,290 | 12/1980 | Montoya et al. | |

OTHER PUBLICATIONS

Owen et al., "A Force-Balance Shear Force Instrument", ISA Transactions, vol. 16, No. 3, 1977, pp. 61–66.

*Primary Examiner*—Charles A. Ruehl
*Attorney, Agent, or Firm*—Howard J. Osborn; John R. Manning

[57] ABSTRACT

A skin friction force measuring device having a first pivoted 13 L-shaped arm 12, a second arm 16 pivoted 17 on one end of the L-shaped arm with a sensing element 20 attached to an end of the second arm. In response to skin friction forces on the sensing element 20 the arms are pivoted about the two pivots and two nulling means 23, 28 force the pivots back to their zero positions. The outputs of the two nulling means are indicative of the skin friction forces along two perpendicular axes, x and y, in the plane of the sensing element.

9 Claims, 6 Drawing Figures

TWO-AXIS, SELF-NULLING SKIN FRICTION BALANCE

ORIGIN OF THE INVENTION

The invention described herein was made by employees of the United States Government and may be used by or for the Government for governmental purposes without the payment of any royalties thereon or therefor.

BACKGROUND OF THE INVENTION

The invention relates generally to skin friction force measuring devices and more specifically concerns a device for measuring skin friction forces along two perpendicular axes in a plane.

In the past, two single-axis balances mounted at a right angle with each other were required to measure skin friction forces in a plane. The major disadvantage for that approach is that the two readings obtained correspond to skin friction forces at two distinct locations.

It is therefore the primary object of this invention to provide a device for measuring, at one location, skin friction forces in a plane along two perpendicular axes.

Another object of this invention is to provide a two-axes, self-nulling skin friction balance that allows free plane motion of the sensing element with no friction.

A further object of this invention is to provide a two-axes, self-nulling skin friction balance that allows relative movements of the nulling components only in their intended axis of operation.

Still another object of this invention is to provide a two-axes, self-nulling skin friction balance to continuously provide direct plane skin friction force measurements at one location.

Other objects and advantages of this invention will become apparent hereinafter in the specification and drawings.

SUMMARY OF THE INVENTION

The invention is a device for measuring the skin friction forces, along two perpendicular axes in the plane of a sensing element, caused by the flow of a fluid into the surface of the sensing element. An L-shaped arm is pivoted on a fixed pivot and a straight second arm is pivoted on an end of the L-shaped arm such that the pivots are in a plane parallel to the sensing element which is attached to the other end of the second arm. A first nulling means detects any movement about the fixed pivot and forces the L-shaped arm back into its zero position. A second nulling means detects any movement of the second arm about its pivot and forces it back into its zero position. The outputs of the two nulling means are indicative of the friction forces along the two perpendicular axes in the plane of the sensing element.

DETAILED DESCRIPTION OF THE INVENTION

Figure 3:
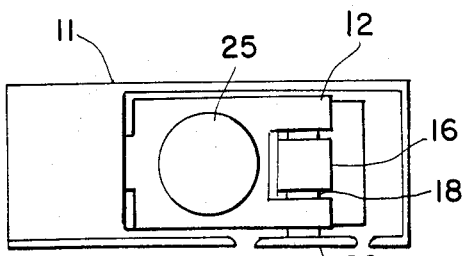
FIG. 3 is a rear side view of FIG. 1.
Figure 4:
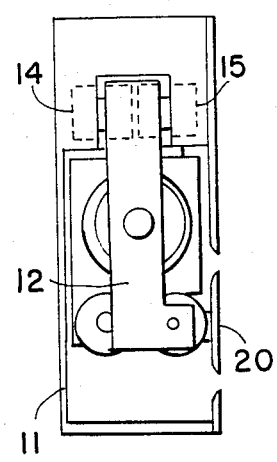
FIG. 4 is a left side view of FIG. 1.

Turning now to the embodiment of the invention selected for illustration in the drawings the number 11 designates a case in which the invention is mounted. For clarity, a case should be interpreted as any object in which the invention is mounted. An L-shaped arm 12 is pivoted about a pivot point 13 by means of two flexural pivots 14 and 15. Pivot point 13 is fixed relative to case 11 and allows arm 12 to be pivoted back and forth in the plane of arm 12. An arm 16 is pivoted on an end of arm 12 about a pivot point 17 by means of a flexural pivot 18. Pivot point 17 allows arm 16 to pivot back and forth in the plane of arm 12 and 16. Inasmuch as the end of arm 12 on which arm 16 is mounted, is movable relative to case 11, pivot point 17 is a floating pivot point relative to case 11. A sensing element 20 is attached to the non-pivoted end of arm 16 such that the plane of sensing element 20 is parallel to the plane of the movements of arms 12 and 16 about pivot points 13 and 17.

A linear-variable-differential-transformer (LVDT) 21 fixed relative to case 11 has its probe 22 attached to arm 12 such that probe 22 will move back and forth in the LVDT 21 with the movements of arm 12 in the x-direction as denoted on sensing element 20. With pivot 13 in its normal or zero position, probe 22 will be positioned inside LVDT 21 causing LVDT 21 to produce a zero position output. Any other position of pivot 13 will reposition probe 22 such that LVDT 21 will produce a signal indicating the movement of arm 12. A force motor 23 has its coil 24 mounted on case 11 and its magnet 25 mounted on arm 12. Whenever there is any movement of arm 12, LVDT 21 will produce a signal which is applied to coil 24 to force arm 12 back into its zero position. An LVDT 26 fixed relative to case 11 has its probe 27 attached to arm 16 to sense any movement of arm 16 in the y-direction. A force motor 28 has its coil 29 mounted on arm 12 and its magnet 30 mounted on arm 16. Whenever there is any movement of arm 16 in the y-direction, LVDT 26 will produce a signal that is applied to coil 29 to force arm 16 back into the zero position.

Figure 1:
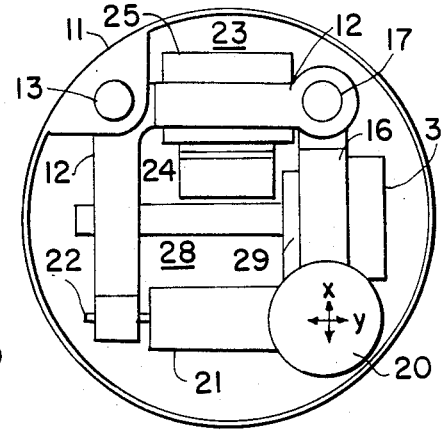
FIG. 1 is a schematic plan view of a preferred embodiment of the invention.
Figure 5:
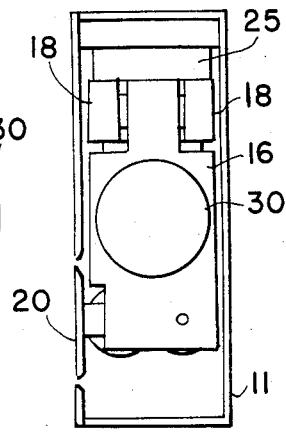
FIG. 5 is a right side view of FIG. 1.
Figure 2:
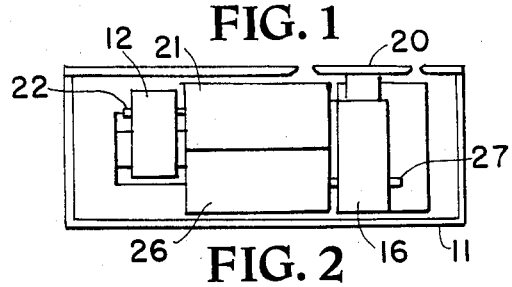
FIG. 2 is a front side view of FIG. 1.
Figure 6:
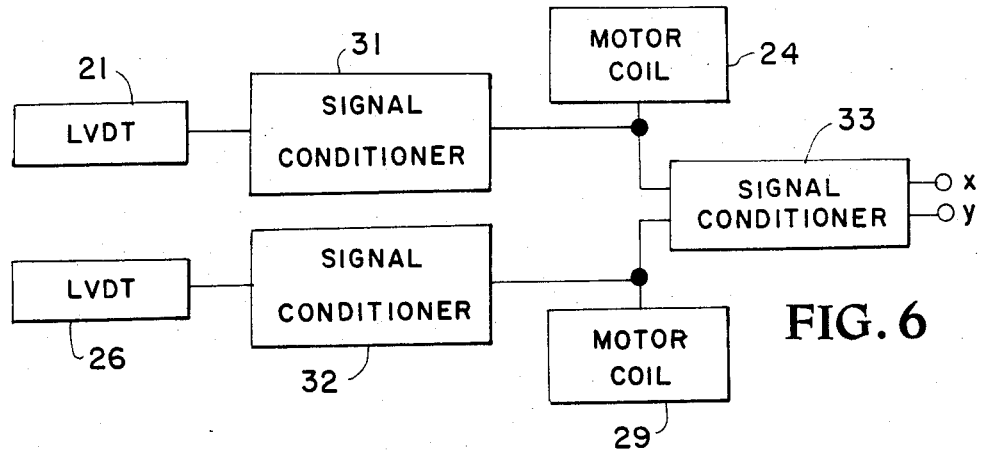
FIG. 6 is a block diagram of the electrical circuit used in the preferred embodiment of the invention.

As shown in FIG. 6 the signals at the outputs of LVDTs 21 and 26 are applied to signal conditioners 31 and 32 before they are applied to motor coils 24 and 29, respectively. The signals to motor coils 24 and 29 are also applied to a signal conditioner 33 to produce output signals which are indicative of the x and y skin friction forces. As can be seen FIG. 1 whenever there is a skin friction force in the y-direction coil 29 forces arm 16 back to its zero position. To do this a force is exerted against arm 12 which will cause LVDT 21 to produce a false signal. To compensate for this false signal a portion of the signal produced by LVDT 26 is subtracted from the signal produced by LVDT 21 by means of a signal conditioner 33 to make the LVDT 21 signal equal to zero. The portion of the LVDT 26 signal subtraced from the LVDT 21 signal is determined by calibration.

In the operation of the invention, air or any other fluid flows into sensing element 20. The resulting skin friction force in the x-direction pivots arm 12 about pivot 13. This movement of arm 12 causes LVDT 21 to produce a signal that is applied to motor coil 24 to force arm 12 back into its zero position. The signal to motor coil 24 is also conditioned by signal conditioner 33 to produce the x output signal indicative of the skin friction force in the x-direction. The skin friction force in the y-direction caused by the air flow pivots arm 16 about pivot 17. This movement of arm 16 causes LVDT 26 to produce a signal that is applied to motor coil 29 to force arm 16 back into its zero position. The signal applied to motor coil 29 is also conditioned by signal conditioner 33 to produce the y output signal indicative of the skin friction force in the y-direction.

A prototype design of this invention has diameter of 1.25 inches, a height of 0.5 inches and a 0.37 inch diameter sensing element.

The advantages of this invention are that it provides a simple inexpensive device for continuously measuring, at one location, skin friction forces in a plane along two perpendicular axes; it allows free plane motion of the sensing element with no friction; and it allows relative movements of the nulling components in their intended axis of operation.

It is to be understood that the form of the invention herewith shown and described is to be taken as a preferred embodiment. Various changes can be made without departing from the invention. For example, nulling means other than LVDTs and force motors could be used and the invention can be used to measure skin friction forces caused by the flow of any fluid.

What is claimed as new and desired to be secured by Letters Patent of the United States is:

1. A two-axes, self-nulling skin friction balance comprising:
   a case;
   a first arm pivoted on said case such that a first end of said arm can move back or forth in a first direction;
   a second arm with a first of its ends pivoted on said first end of said first arm such that the second end of said second arm can move back or forth in a second direction in the plane of said first direction;
   a sensing plate mounted on said second end of said second arm in a plane parallel to said plane of said first and second directions;
   a first nulling means for sensing any movement of said first arm from its zero position and forcing it back to its zero position;
   a second nulling means for sensing any movement of said second arm from its zero position and forcing it back to its zero position; and
   means for processing the sensing outputs of said first and second nulling means to obtain the skin friction forces on said sensing plate in said first and second directions.

2. A two axes, self-nulling skin friction balance according to claim 1 wherein said first and second arms are pivoted by means of flexural pivots.

3. A two axes, self-nulling skin friction balance according to claim 1 wherein said first arm comprising a first section and a second section with the two sections joined to form an L and with said first arm pivoted where the two sections join, and with the said first end of the first arm being the free end of said first section.

4. A two axes, self-nulling skin friction balance according to claim 3 wherein said first nulling means comprises sensing means for sensing the movement of said first arm and force means receiving sensing signals from said sensing means for forcing said first arm back into its zero position.

5. A two axes, self-nulling skin friction balance according to claim 4 wherein said second nulling means comprises sensing means for sensing the movement of said second arm and force means mounted on the said second section of said first arm receiving sensing signals from said sensing means for forcing said second arm back into its zero position.

6. A two axes, self-nulling skin friction balance according to claim 5 wherein said sensing means for said first and second nulling means are LVDTs.

7. A two axes, self-nulling skin friction balance according the claim 6 wherein said forces means for said first and second nulling means are force motors.

8. A two axes, self-nulling skin friction balance comprising:
   a sensing plane surface;
   a first pivoting means for pivoting said sensing plane surface such that it will move back or forth on a first axis in said sensing plane surface in response to skin friction forces along said first axis;
   a second pivoting means for pivoting said first pivoting means and said sensing plane surface such that the sensing plane surface will move back and forth on a second axis in said sensing plane surface in response to skin friction forces along said second axis;
   a first nulling means for sensing the movement along said first axis and forcing the sensing plane surface back to its zero position;
   a second nulling means for sensing the movement along said second axis and forcing the sensing plane surface back to its zero position; and
   means for processing the outputs from said first and second nulling means to obtain the skin friction forces along said first and second axes.

9. A method for measuring the skin friction forces along two axes on a sensing surface comprising the steps of:
   independently pivoting a sensing plane surface back or forth about a first pivot point along a first axis in the sensing plane surface in response to a skin friction force along said first axis;
   independently pivoting said sensing plane surface back or forth about a second pivot point pivotally connected to the first pivot point along a second axis in the sensing plane surface in response to a skin friction force along said second axis;
   forcing said sensing plane surface back to its zero position along said first axis in response to any movement along said first axis;
   forcing said sensing plane surface back to its zero position along said second axis in response to any movement along said second axis; and
   processing the forces applied to the sensing plane surface to move it back to its zero positions to obtain the skin friction forces along said first and second axes.

* * * * *